US011793735B2

(12) United States Patent
Hilliard, Jr. et al.

(10) Patent No.: US 11,793,735 B2
(45) Date of Patent: *Oct. 24, 2023

(54) ALUMINUM-FREE ANTIPERSPIRANT / DEODORANT COMPOSITIONS

(71) Applicant: Colgate-Palmolive Company, New York, NY (US)

(72) Inventors: Peter Hilliard, Jr., Far Hills, NJ (US); Sharon Kennedy, Randallstown, MD (US); Cristina Bielli, Hillsborough, NJ (US); Richard Adams, South Orange, NJ (US)

(73) Assignee: Colgate-Palmolive Company, New York, NY (US)

( * ) Notice: Subject to any disclaimer, the term of this patent is extended or adjusted under 35 U.S.C. 154(b) by 404 days.

This patent is subject to a terminal disclaimer.

(21) Appl. No.: 16/468,754

(22) PCT Filed: Dec. 8, 2017

(86) PCT No.: PCT/US2017/065222
§ 371 (c)(1),
(2) Date: Jun. 12, 2019

(87) PCT Pub. No.: WO2018/111704
PCT Pub. Date: Jun. 21, 2018

(65) Prior Publication Data
US 2020/0016053 A1   Jan. 16, 2020

Related U.S. Application Data

(60) Provisional application No. 62/434,219, filed on Dec. 14, 2016.

(51) Int. Cl.
| | |
|---|---|
| *A61K 8/27* | (2006.01) |
| *A61K 8/06* | (2006.01) |
| *A61K 8/34* | (2006.01) |
| *A61K 8/39* | (2006.01) |
| *A61K 8/85* | (2006.01) |
| *A61K 8/92* | (2006.01) |
| *A61K 8/86* | (2006.01) |
| *A61K 8/19* | (2006.01) |
| *A61K 8/44* | (2006.01) |
| *A61Q 15/00* | (2006.01) |

(52) U.S. Cl.
CPC ............... *A61K 8/27* (2013.01); *A61K 8/062* (2013.01); *A61K 8/345* (2013.01); *A61K 8/39* (2013.01); *A61K 8/85* (2013.01); *A61K 8/922* (2013.01); *A61Q 15/00* (2013.01); *A61K 2800/30* (2013.01); *A61K 2800/596* (2013.01)

(58) Field of Classification Search
CPC .................. A61K 8/27; A61K 2800/30; A61K 2800/596; A61K 8/062; A61K 8/345; A61K 8/39; A61K 8/85; A61K 8/86; A61K 8/922; A61K 8/06; A61K 8/19; A61K 8/34; A61K 8/44; A61K 8/92; A61Q 15/00

See application file for complete search history.

(56) References Cited

U.S. PATENT DOCUMENTS

| | | |
|---|---|---|
| 4,722,835 A | 2/1988 | Schamper et al. |
| 4,777,034 A | 10/1988 | Olivier |
| 5,258,174 A | 11/1993 | Schebece |
| 5,512,274 A | 4/1996 | Phinney |
| 6,358,499 B2 | 3/2002 | Hall-Puzio et al. |
| 6,538,499 B1 | 3/2003 | Lu |
| 6,558,710 B1 | 5/2003 | Godfrey |
| 6,713,051 B2 | 3/2004 | Mayes et al. |
| 6,884,409 B2 | 4/2005 | Klug et al. |
| 7,976,828 B2 | 7/2011 | Popoff et al. |
| 8,563,754 B2 | 10/2013 | Orlow et al. |
| 9,314,412 B2 | 4/2016 | Phinney |
| 9,707,171 B2 | 7/2017 | Fan et al. |
| 9,750,670 B2 | 9/2017 | Pan et al. |
| 9,757,316 B2 | 9/2017 | Pan et al. |
| 9,827,177 B2 | 11/2017 | Yuan et al. |
| 10,864,147 B2 * | 12/2020 | Hilliard, Jr. ............... A61K 8/86 |
| 2003/0049290 A1 * | 3/2003 | Jha .......................... A61Q 15/00 424/401 |
| 2003/0206973 A1 | 11/2003 | Gale |
| 2005/0203179 A1 * | 9/2005 | Banowski ............... A61Q 15/00 514/718 |
| 2011/0030083 A1 | 2/2011 | Fowler |
| 2015/0050227 A1 * | 2/2015 | Liu ........................... A61Q 15/00 424/66 |

(Continued)

FOREIGN PATENT DOCUMENTS

| | | |
|---|---|---|
| CN | 1111983 | 11/1995 |
| CN | 1732889 | 2/2006 |

(Continued)

OTHER PUBLICATIONS

International Search Report and Written Opinion of the International Searching Authority in International Application No. PCT/US2017/065222, dated Mar. 26, 2018.

*Primary Examiner* — Jeffrey T. Palenik

(57) ABSTRACT

An aluminum-free antiperspirant/deodorant composition is disclosed. The antiperspirant/deodorant may include an oil-in-water emulsion base and an antiperspirant active dispersed in the oil-in-water emulsion base. The antiperspirant active may be primarily a zinc-based antiperspirant active and the oil-in-water emulsion base may include an emulsifier comprising a mixture of steareth-2 and steareth-20; a plant-based oil, a polyol, and water.

17 Claims, No Drawings

(56) References Cited

U.S. PATENT DOCUMENTS

2015/0118173 A1    4/2015  Farwick et al.
2021/0059913 A1*   3/2021  Hilliard, Jr. .............. A61K 8/39

FOREIGN PATENT DOCUMENTS

| CN | 101022778   | 8/2007  |
|----|-------------|---------|
| CN | 101163523   | 4/2008  |
| CN | 101360464   | 2/2009  |
| CN | 101406429   | 4/2009  |
| CN | 102228419   | 11/2011 |
| CN | 102802732   | 11/2012 |
| CN | 104284651   | 1/2015  |
| CN | 104853812   | 8/2015  |
| CN | 104873442   | 9/2015  |
| CN | 105473124   | 4/2016  |
| CN | 105792799   | 7/2016  |
| CN | 105792896   | 7/2016  |
| EP | 1736135     | 12/2006 |
| JP | 5496564     | 5/2014  |
| RU | 2179015     | 2/2002  |
| WO | 2006/023882 | 3/2006  |
| WO | 2006/119981 | 11/2006 |
| WO | 2013/052454 | 4/2013  |
| WO | 2014/092688 | 6/2014  |

* cited by examiner

ALUMINUM-FREE ANTIPERSPIRANT / DEODORANT COMPOSITIONS

BACKGROUND

Current roll-on antiperspirant/deodorant products in the market are usually emulsions which employ the suspension of an antiperspirant active in the formulation. Various metallic salts, for example, of zinc, iron, and aluminum, have been used as antiperspirant actives, with chlorohydrates and chlorides of aluminum and zirconium being the most commonly used antiperspirant active. However, there is a growing desire to replace these salts with other active metal salts. Zinc, which has antibacterial properties, has been explored as a possible candidate to replace aluminum. However, Phinney in U.S. Pat. No. 5,512,274 reported that zinc salts precipitate as hydroxides in the range of pH of 6.5 to 8.0, and have been shown to behave erratically, being effective as an antiperspirant only for very irregular periods of time, which makes them undependable. The sporadic efficacy of zinc salts was speculated to be due to various factors, such as lack of hydrolysis conversion to relatively inactive carbonate or oxide, or some other factor or combination of factors.

Yuan and Pan, in U.S. patent publication no. 2015/0313821, reported that zinc oxide is weakly soluble at low pH. However, due to human perspiration having a pH of 5-6, the perspiration can reduce the levels of precipitation of the zinc oxide compared to precipitation levels at neutral pH. Moreover, the perspiration can gradually dissolve the depositions, reducing the duration of action of the formulation.

Hence, there remains a desire for a deodorant and/or antiperspirant/deodorant composition with increased substantivity of zinc on a skin surface.

BRIEF SUMMARY

Disclosed herein is an antiperspirant/deodorant composition comprising: an oil-in-water emulsion base comprising: an emulsifier comprising a mixture of steareth-2 and steareth-20, a plant-based oil, a polyol, water; and an antiperspirant active dispersed in the oil-in-water emulsion base, wherein the antiperspirant active consists essentially of a zinc-based antiperspirant active.

In an embodiment of the antiperspirant/deodorant composition, the zinc-based antiperspirant active comprises one or more of zinc oxide, zinc hydroxide, zinc hydroxide ions with counter ions, and zinc ions with counter ions.

In another embodiment of the antiperspirant/deodorant composition, the antiperspirant/deodorant composition is essentially free of aluminum-based antiperspirant actives, magnesium-based actives; and calcium-based actives.

In one embodiment of the antiperspirant/deodorant composition, the zinc-based antiperspirant active is present in an amount of from 0.5 to 10 weight %, based on the total amount of the antiperspirant/deodorant composition.

In another embodiment of the antiperspirant/deodorant composition, the emulsifier is present in an amount of from 0.5 to 5 weight %, based on the total amount of the antiperspirant/deodorant composition.

In yet another embodiment of the antiperspirant/deodorant composition, the emulsifier further comprises one or more of steareth-2, steareth-4, ceteareth-2, ceteareth-3, ceteareth-4, ceteareth-18, ceteareth-20, and ceteareth-22.

In one embodiment of the antiperspirant/deodorant composition, the emulsifier consists essentially of a mixture of steareth-2 and steareth-20, and wherein steareth-2 and steareth-20 are present in a weight ratio of 2.2:1 to 2.5:1.

In another embodiment of the antiperspirant/deodorant composition, the emulsifier may comprise one or more of steareth-2, steareth-20, and steareth-21.

In one embodiment of the antiperspirant/deodorant composition, the antiperspirant/deodorant composition further comprises a silicone based emollient present in an amount of from 0.1 to 6 weight %, based on the total amount of the antiperspirant/deodorant composition.

In another embodiment of the antiperspirant/deodorant composition, the antiperspirant/deodorant composition further comprises a non-silicone based emollient present in an amount of from 0.1 to 6 weight %, based on the total amount of the antiperspirant/deodorant composition.

In yet another embodiment of the antiperspirant/deodorant composition, the non-silicone based emollient comprises one or more of isopropyl myristate, isopropyl palmitate, isopropyl stearate, isopropyl isostearate, butyl stearate, octyl stearate, hexyl laurate, cetyl stearate, diisopropyl adipate, isodecyl oleate, diisopropyl sebacate, isostearyl lactate, $C_{12}$-$C_{15}$ alkyl benzoate, myreth-3 myristate, dioctyl malate, neopentyl glycol diheptanoate, dipropylene glycol dibenzoate, $C_{12}$-$C_{15}$ alcohols lactate, isohexyl decanoate, isohexyl caprate, diethylene glycol dioctanoate, octyl isononanoate, isodecyl octanoate, diethylene glycol diisononanoate, isononyl isononanoate, isostearyl isostearate, behenyl behenate, $C_{12}$-$C_{15}$ alkyl fumarate, laureth-2 benzoate propylene glycol isoceteth-3 acetate, propylene glycol ceteth-3 acetate, octyldodecyl myristate, and cetyl recinoleate, myristyl myristate, lanolate, paraffin waxes, glycyrrhizic acid, and hydrocyethyl stearate amide.

In one embodiment of the antiperspirant/deodorant composition, the non-silicone based emollient comprises diisopropyl adipate, neopentyl glycol diethylene hexanoate, and mixtures thereof.

In an embodiment of the antiperspirant/deodorant composition, the plant-based oil comprises one or more of sunflower oil, soybean oil, corn oil, jojoba oil, and methyl and/or ethyl ester derivatives thereof.

In an embodiment of the antiperspirant/deodorant composition, the plant-based oil comprises one or more of sunflower oil, soybean oil, corn oil, jojoba oil, and methyl and/or ethyl ester derivatives thereof.

In another embodiment of the antiperspirant/deodorant composition, the plant-based oil comprises a partially hydrogenated soybean oil in an amount of 5% or less by weight.

In an embodiment of the antiperspirant/deodorant composition, the oil-in-water emulsion base further comprises at least one of a mineral oil and a synthetic oil.

In yet another embodiment, the antiperspirant/deodorant composition further comprises a substantivity enhancer of the zinc-based antiperspirant active, wherein the substantivity enhancer is a film-forming polymer composition comprising at least one of a mixture of polyester-10 and propylene glycol dibenzoate; a mixture of polyester-7 and neopentyl glycol diheptanoate; adipic acid/diglycol crosspolymer; trimethylpentanediol/adipic acid/glycerin crosspolymer; trimethylpentanediol/adipic acid copolymer; capryloyl glycerin/sebacic acid copolymer; and PVM/MA decadiene crosspolymer.

In one embodiment of the antiperspirant/deodorant composition, the antiperspirant/deodorant composition provides substantive zinc in an amount of at least 8 picoMoles per 0.34 $cm^2$ of a skin surface, as measured by the method disclosed herein.

In an aspect, there is a method of reducing apparent perspiration comprising applying the antiperspirant/deodorant composition as disclosed hereinabove to an axillary area of a person, wherein the antiperspirant/deodorant composition of claim 1 reduces apparent perspiration.

In another aspect, there is a method and/or use of any one or more of the antiperspirant/deodorant compositions disclosed herein to reduce stinging, burning, and/or tingling of the skin.

In another aspect, there is a use of the antiperspirant/deodorant composition as disclosed hereinabove to increase substantivity of zinc on a skin surface, when tested using a method as disclosed herein.

In yet another aspect, there is a use of a zinc substantivity enhancer in the antiperspirant/deodorant composition as disclosed hereinabove to increase substantivity of zinc on a skin surface when applied to an axillary area of an armpit, wherein the substantivity enhancer is a film-forming polymer composition comprising at least one of a mixture of polyester-7 and neopentyl glycol diheptanoate; adipic acid/diglycol crosspolymer; trimethylpentanediol/adipic acid/glycerin crosspolymer; trimethylpentanediol/adipic acid copolymer; capryloyl glycerin/sebacic acid copolymer; and PVM/MA decadiene crosspolymer.

Further areas of applicability of the present invention will become apparent from the detailed description provided hereinafter. It should be understood that the detailed description and specific examples, while indicating some preferred aspects of the invention, are intended for purposes of illustration only and are not intended to limit the scope of the invention.

DETAILED DESCRIPTION

The following description of various preferred aspect(s) is merely exemplary in nature and is in no way intended to limit the invention, its application, or uses.

As used throughout, ranges are used as shorthand for describing each and every value that is within the range as well as the endpoints. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

As used herein, the term "antiperspirant/deodorant compositions" refers to compositions which exhibit at least one of an antiperspirant effect or both an antiperspirant effect and a deodorant effect.

As used herein, the terms "zinc substantivity" and "substantivity of zinc" are used interchangeably and refer to adsorption and retention of zinc, for example in the form of zinc oxide, zinc hydroxide, zinc hydroxide ions, and/or zinc ions, on or within the top layers of a surface, such as a skin surface, and once there, resistance to subsequent removal or rinsing off of the zinc during rinsing procedure performed five times with 100 µl of 0.1 M NaCl solution to simulate perspiration or sweating.

As used herein, the term "zinc substantivity enhancer" refers to a film-forming polymer that when used in a composition containing zinc (e.g., zinc oxide) increases the substantivity of zinc on a skin surface as compared to a comparative composition without the film-forming polymer.

Compositions

The antiperspirant/deodorant compositions of the present disclosure can be a liquid, a cream, or a gel. In the liquid form, the composition can be formulated to be a roll-on antiperspirant/deodorant. In one embodiment, the composition may be an oil-in-water liquid emulsion. In some embodiments or aspects, the liquid composition can be contained in any roll-on dispenser that has a ball or the like or a domed surface, for applying the antiperspirant/deodorant composition to the surface of the skin. In some other aspects, the liquid composition can be contained in an aerosol or pump spray dispenser, or a cream/gel dispenser.

In an aspect, there may be an antiperspirant/deodorant composition that may include an oil-in-water emulsion base and an antiperspirant active dispersed in the oil-in-water emulsion base, the antiperspirant active consisting essentially of a zinc-based antiperspirant active. The zinc-based antiperspirant active may include one or more of zinc oxide, zinc hydroxide, zinc hydroxide ions with counter ions, and zinc ions with counter ions, such as, for example, ZnO, $Zn^{2+}(aq)$, $Zn(OH)^+(aq)$, $Zn(OH)_2(aq)$, $Zn(OH)^-(aq)$, and $Zn(OH)^{2-}(aq)$. Non-limiting examples of counter ions may include, halides, carboxylate based fatty acid salt, amino acid salt, cationic surfactants, zwitterionic surfactant, etc.

In some variations of the composition, the oil-in-water emulsion base may include water and an emulsifier that may include or may be a mixture of steareth-2 and steareth-20 or a mixture of steareth-2 and steareth-21, a non-silicone based emollient, a plant-based oil, and a polyol. In other variations of the composition, the oil in water emulsion base may include water and an emulsifier that may include or may be a mixture of streareth-2 and steareth-20 or a mixture of steareth-2 and steareth-21, a silicon based emollient, a plant-based oil, and a polyol.

In one aspect, the antiperspirant effect of the antiperspirant/deodorant compositions of the present disclosure may be provided by a zinc-based antiperspirant active, which may be zinc oxide, zinc hydroxide, zinc hydroxide ions with counter ions, and zinc ions with counter ions and/or mixtures thereof, rather than by an aluminum-based antiperspirant active. Thus, the antiperspirant/deodorant compositions described in the present disclosure may be essentially free of added: aluminum-based antiperspirant actives, magnesium-based actives such as, for example, magnesium salts and magnesium hydroxide, and calcium-based actives such as, for example, calcium salts and calcium hydroxide. In another aspect, the antiperspirant/deodorant compositions described herein may include at least one of aluminum-based antiperspirant actives, magnesium-based actives such as, for example, magnesium salts and magnesium hydroxide, and calcium-based actives such as, for example, calcium salts and calcium hydroxide.

By the term "essentially free of added aluminum-based antiperspirant actives, magnesium-based actives, and calcium-based actives", it is meant that aluminum-based antiperspirant actives, magnesium-based actives, and calcium-based actives may not be added to the antiperspirant/deodorant composition in an amount that could display some antiperspirant/deodorant effect. However, aluminum-based antiperspirant actives, magnesium-based actives, and calcium-based actives may be present in small or trace amounts due to contamination from other ingredients used in the making of the antiperspirant/deodorant formulations of the present disclosure. For example, the antiperspirant/deodorant compositions that are essentially free of added aluminum-based antiperspirant actives, magnesium-based actives, and calcium-based actives may include the aluminum-based antiperspirant actives, magnesium-based actives, and calcium-based actives as impurities.

In various embodiments of the antiperspirant and/or deodorant compositions described herein, "essentially free of aluminum-based antiperspirant actives, magnesium-based actives, and calcium-based actives" means that the antiperspirant and/or deodorant compositions of the present disclosure contains less than 0.05 weight %, or less than 0.01 weight % of one or more of aluminum-based antiperspirant actives, magnesium-based actives, and calcium-based actives.

As used herein, the term "aluminum-free" means that the composition does not contain any aluminum-based antiperspirant. Non-limiting examples of aluminum-based antiperspirant actives, may include those listed in US antiperspirant monograph, such as, for example, aluminum chlorohydrate, aluminum chloride, aluminum sesquichlorohydrate, zirconyl hydroxychloride, aluminum-zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly), aluminum chlorohydrex PG, aluminum chlorohydrex PEG, aluminum dichlorohydrex PG, and aluminum dichlorohydrex PEG.

Examples of magnesium-based actives may include, but are not limited to, magnesium chloride, magnesium bromide, magnesium fluoride and organic salts such as various alkyl chain length substituted carboxylic acids, magnesium oxide, and magnesium hydroxide. Examples of calcium-based actives may include, but are not limited to, calcium chloride, calcium bromide, calcium fluoride and organic salts such as various alkyl chain length substituted carboxylic acids, calcium oxide, and calcium hydroxide.

The antiperspirant/deodorant composition of the present disclosure may include an antiperspirant active that may be primarily a zinc-based antiperspirant active present in an amount of from 0.05 to 15 weight %, or 0.1 to 10 weight %, or 0.5 to 10 weight %, based on the total weight of the antiperspirant/deodorant composition. The zinc-based antiperspirant active in the form of zinc oxide can be incorporated into the antiperspirant/deodorant compositions by dispersing zinc oxide in the oil-in-water emulsion base. Zinc oxide present in the antiperspirant/deodorant composition may convert partially to zinc hydroxide or may be present as zinc ions, or zinc hydroxide ions depending upon the pH of the final antiperspirant/deodorant composition. Hence, the amount of zinc oxide initially added to form the antiperspirant/deodorant compositions of the present disclosure may differ from the final amount of zinc oxide present in the composition due to conversion to zinc hydroxide and/or zinc ions depending upon the pH of the final antiperspirant/deodorant composition.

The pH of the antiperspirant/deodorant composition can be in the range of 3 to 10, or 3 to 9, or 4 to 8, or 5 to 8, or the pH can be 9, or 8, or 7, or 6.5, or 6.

Zinc Substantivity Enhancer

The antiperspirant/deodorant compositions of the present disclosure can also include a film-forming polymer to further enhance zinc substantivity on a skin surface. Any suitable film-forming polymer may be used in the antiperspirant/deodorant composition of the present disclosure, including but not limited to, one or more of a mixture of polyester-10 and propylene glycol dibenzoate; a mixture of polyester-7 and neopentyl glycol diheptanoate; adipic acid/diglycol crosspolymer; trimethylpentanediol/adipic acid/glycerin crosspolymer (a copolymer of trimethylpentanediol and adipic acid crosslinked with glycerin); trimethylpentanediol/adipic acid copolymer; capryloyl glycerin/sebacic acid copolymer, and PVM/MA decadiene crosspolymer (a copolymer of maleic anhydride and methyl vinyl ether crosslinked with 1,9-decadiene). Without wishing to be bound by theory, it is believed that the polyester-10 present in the hydrophobic film-forming polymer composition will spread quickly on a skin surface with improved skin feel and limited interaction with the skin. In addition, the highly water-resistant characteristics of the polyester-10 should aid in both increasing substantivity of zinc on a skin surface and also in reducing apparent perspiration by preventing sweat from reaching the skin surface.

In an embodiment, the film-forming polymer composition may be a mixture of polyester-10 and propylene glycol dibenzoate. The mixture of polyester-10 and propylene glycol dibenzoate as a film-forming polymer composition, for use as a zinc substantivity enhancer can be included in any desired amount. In one embodiment, the total amount of the film-forming polymer mixture of polyester-10 and propylene glycol dibenzoate may be in the range of 0.1 to 4.5 weight %, or 0.5 to 4 weight %, or 1.0 to 3.6 weight %, based on the total weight of the antiperspirant/deodorant composition.

The film-forming PVM/MA decadiene crosspolymer, for use as a zinc substantivity enhancer can be included in any desired amount. In one embodiment, the total amount of the film-forming polymer may be in the range of 0.1 to 5 weight %, or 0.2 to 4 weight %, or 0.25 to 3 weight %, based on the total weight of the antiperspirant/deodorant composition. Without wishing to be bound by theory, it is believed that the PVM/MA decadiene crosspolymer will interact with the Zinc in the formulation to create a hydrophobic film on the skin that enhances the water-resistant characteristics of the PVM/MA decadiene crosspolymer and increases the substantivity of zinc on a skin surface and also in reducing apparent perspiration by preventing sweat from reaching the skin surface.

Suitable examples of commercially available film-forming polymer composition may include, but are not limited to a mixture of polyester-10 and propylene glycol dibenzoate available as LexFilm® Spray; a mixture of polyester-7 and neopentyl glycol diheptanoate as LexFilm® Sun; adipic acid/diglycol crosspolymer as Lexorez® 100; trimethylpentanediol/adipic acid/glycerin crosspolymer as Lexorez® 200; trimethylpentanediol/adipic acid copolymer as Lexorez® TL-8; trimethylpentanediol/adipic acid/Glycerin crosspolymer as WetFilm™; capryloyl glycerin/sebacic acid copolymer as Vellaplex™ all from the Inolex Chemical Company of Philadelphia, PA Another suitable example of commercially available film-forming polymer composition may include, PVM/MA decadiene crosspolymer available as APShield™ 100, from the Ashland Specialty Ingredients Company of Bridgewater, NJ and as Stabileze™ QM from Ashland Inc., Covington, KY.

In at least one embodiment, the weight ratio of the film-forming polymer to zinc oxide may be greater than or equal to 0.5:1 and less than or equal to 2.4:1. For example, the weight ratio of the film-forming polymer to zinc oxide may be from about 0.5:1, about 0.6:1, about 0.7:1, about 0.8:1, about 0.9:1, about 1:1, about 1.1:1, about 1.2:1, about 1.3:1, or about 1.4:1 to about 1.5:1, about 1.6:1, about 1.7:1, about 1.8:1, about 1.9:1, about 2:1, about 2.1:1, about 2.2:1, about 2.3:1, or about 2.4:1. In another example, the weight ratio of the film-forming polymer to zinc oxide may be from about 0.5:1 to about 2.4:1, about 0.6:1 to about 2.3:1, about 0.7:1 to about 2.2:1, about 0.8:1 to about 2.1:1, about 0.9:1 to about 2:1, about 1:1 to about 1.9:1, about 1.1:1 to about 1.8:1, about 1.2:1 to about 1.7:1, about 1.3:1 to about 1.6:1, or about 1.4:1 to about 1.5:1.

Oil-in-Water Emulsion Base

The antiperspirant/deodorant compositions of the present disclosure may include an oil-in-water emulsion base. The oil-in-water emulsion base may include an emulsifier that may include a mixture of steareth-2 and steareth-20 or a mixture of steareth-2 and steareth-21, a non-silicone based emollient, a plant-based oil, a polyol, and water. The oil-in-water emulsion base may also include an emulsifier that may include a mixture of steareth-2 and steareth-20 or a mixture of steareth-2 and steareth-21, a silicone based emollient, a plant-based oil, a polyol, and water.

Emulsifiers

The oil-in-water emulsion base of the antiperspirant/deodorant composition of the present disclosure may include a mixture of steareth-2 and steareth-20 or a mixture of steareth-2 and steareth-21. Steareth-2 and Steareth-20 may be polyoxyethylene stearyl ethers having chemical formula: $CH_3-(CH_2)_{16}-CH_2-(O-CH_2-CH_2)_n-OH$ with average n being 2 or 20 respectively. However, any other suitable emulsifier can also be present in the oil-in-water emulsion base of the antiperspirant/deodorant composition. The emulsifiers can be included in any desired amount. In one embodiment, the total amount of emulsifier (Steareth-2 and Stearath-20) may be in the range of 0.5 to 12 weight %, or 0.5 to 10 weight %, based on the total weight of the composition.

Suitable emulsifiers may include, but are not limited to, Steareth-2, Steareth-4, Steareth-20, Steareth-21, Ceteareth-2, Ceteareth-3, Ceteareth-4, Ceteareth-18, Ceteareth-20, Ceteareth-22. In an embodiment, the oil-in-water base composition may include a combination of two surfactants, one having an HLB (hydrophilic-lipophilic balance) value of 2 to 8 (such as Steareth-2) and the other having an HLB of 9 to 18 (such as Steareth-20 or Steareth-21). In one embodiment, the emulsifier present in the antiperspirant/deodorant composition of the present disclosure may be primarily or essentially a mixture of steareth-2 and steareth-20. In such embodiments, the steareth-2 and steareth-20 may be present in a weight ratio of 2.2:1 to 2.5:1, or 1:1 to 1.75:1, or 1:1 to 1.2:1.

Steareth-2 and Steareth-20 may be polyoxyethylene stearyl ethers having chemical formula: $CH_3-(CH_2)_{16}-CH_2-(O-CH_2-CH_2)_n-OH$ with average n being 2 or 20 respectively. It has been a surprising discovery that steareth-2 has been found to have a positive effect on increasing the zinc substantivity and comparison steareth-20 has been found to have a negative effect on the zinc substantivity. Without wishing to be bound by theory, it is believed that it is the difference in the balance of hydrophilic and lipophilic parts of Steareth-2 and Steareth-20 that results in opposite effect. Steareth-2 with short ethylene oxide chain may be a water-in-oil emulsifier, as the hydrophilic part may be smaller than and subordinate to the lipophilic part. The relatively longer lipophilic part of Steareth-2 is believed to help in an increase in zinc substantivity.

Non-Silicone Based Emollient

The antiperspirant/deodorant composition can contain any suitable non-silicone based emollient in any desired amount to achieve a desired emollient effect. In one embodiment, the amount of emollients may be less than 15%, or less than 11%, or in the range of 0.1 to 8 weight % or 0.1 to 6 weight %, based on the total weight of the composition. Emollients may be known in the art and may be used to impart a soothing effect on the skin.

Suitable non-silicone based emollients may be selected from among isopropyl myristate, isopropyl palmitate, isopropyl stearate, isopropyl isostearate, butyl stearate, octyl stearate, hexyl laurate, cetyl stearate, diisopropyl adipate, isodecyl oleate, diisopropyl sebacate, isostearyl lactate, $C_{12}$-$C_{15}$ alkyl benzoate, myreth-3 myristate, dioctyl malate, neopentyl glycol diheptanoate, dipropylene glycol dibenzoate, $C_{12}$-$C_{15}$ alcohols lactate, isohexyl decanoate, isohexyl caprate, diethylene glycol dioctanoate, octyl isononanoate, isodecyl octanoate, diethylene glycol diisononanoate, isononyl isononanoate, isostearyl isostearate, behenyl behenate, $C_{12}$-$C_{15}$ alkyl fumarate, laureth-2 benzoate propylene glycol isoceteth-3 acetate, propylene glycol ceteth-3 acetate, octyldodecyl myristate, and cetyl recinoleate, myristyl myristate, isopropyl, lanolate, paraffin waxes, glycyrrhizic acid, and hydrocyethyl stearate amide.

In an embodiment, the non-silicone based emollient comprises one or more of diisopropyl adipate and neopentyl glycol diethylene xanoate.

Silicone Based Emollient

The antiperspirant/deodorant composition can also contain any suitable silicone based emollient in any desired amount to achieve a desired emollient effect. In one embodiment, the amount of emollients may be less than 15%, or less than 11%, or in the range of 0.1 to 8 weight % or 0.1 to 6 weight %, based on the total weight of the composition. Emollients may be known in the art and may be used to impart a soothing effect on the skin. Illustrative silicone based emollients may be or may include, but are not limited to, silicones, such as dimethicone, dimethiconol, cyclopentasiloxane. phenyl trimethicone, cyclomethicone, and the like, and mixtures and combinations thereof. Additional, non-limiting examples of silicon and non-silicone based emollients may be found in U.S. Pat. No. 6,007,799, the contents of which may be incorporated herein in its entirety. Further illustrative examples of silicon based emollients may be well known among those skilled in the art.

Polyols

The polyol may be selected from among ethylene glycol, propylene glycol, 1,2-propanediol, diethylene glycol, triethylene glycol, tetraethylene glycol, dipropylene glycol, tripropylene glycol, methyl propanediol, 1,6-hexanediol, 1,3-butanediol, 1,4-butanediol, 1,2-octanediol (capryl glycol), PEG-4 through PEG-100, PPG-9 through PPG-34, pentylene glycol, neopentyl glycol, trimethylpropanediol, 1,4-cyclohexanedimethanol, 2,2-dimethyl-1,3-propanediol, 2,2,4,4-tetramethyl-1,3-cyclobutanediol, and mixtures thereof. More particular examples of the glycol component may include one or more of propylene glycol, dipropylene glycol, tripropylene glycol, 2-methyl-1,3-propanediol, methyl propylene glycol, low molecular weight (less than 600) polyethylene glycol, low molecular weight (less than 600) polypropylene glycols, and mixtures of any of the foregoing. Mixtures of glycols may be used. In an embodiment, the oil-in-water emulsion base of the present antiperspirant/deodorant composition comprises 1,2-octanediol (capryl glycol). The polyol maybe present in any suitable amount, such as in the range of 0.2 to 0.3 weight %, or 0.2 to 0.4 weight %, or 0.2 to 0.6 weight %, or 0.2 to 0.9 weight %, based on the total weight of the composition.

Plant-Based Oils

In various embodiments, the antiperspirant and/or deodorant compositions disclosed herein may include a plant-based oil having a melting point of −15 to 38° C., which may be an oil that may be obtained from a plant or may be a synthetically manufactured equivalent. These can include common triglycerides such as sunflower oil, soybean oil, corn oil as non-limiting examples. As used herein, the term oil may include materials that may be defined as a liquid wax. For example, jojoba oil can be referred to as a liquid wax. The methyl and ethyl esters of plant-derived oils may also be included in the definition of a plant-derived oil. This plant-derived oil can provide structure to the composition, and thus, yield to suspend materials with densities significantly different from the emulsion base. In one embodiment, this material may be present in an amount of 5% or less by weight of the composition. Levels much higher than 5% may give an oily/greasy feel to the composition and cause an undesirable increase in drying time on the skin. In one embodiment, the amount of plant-derived oil may be 1 to 5% by weight of the composition. Examples of the plant-derived oil may include, but are not limited to, soybean oil, jojoba oil, coconut oil, safflower oil, palm kernel oil, cottonseed oil, and pine nut oil. In certain embodiments, the plant-derived oils may be partially hydrogenated versions of these oils. Lower levels of unsaturation, such as high oleic sunflower oil verses normal sunflower oil, can reduce potential chemical interaction with other roll-on components and can also reduce the tendency for the oil to oxidize and form a rancid odor that may be harder to fragrance. The iodine value and percent saturates (which may be inversely proportional to each other) may be two means of describing the degree of hydrogenation present in the plant-derived oil.

One of the advantages of the presence of the plant-derived oil in the antiperspirant/deodorant composition is that the plant-derived oils reduces the tackiness of the antiperspirant active, which may be found in the aqueous phase. The addition of non-silicon based emollients in combination with the plant-derived oil can also give this desired effect when the total amount of emollient and the plant-derived oil may be less than 7 weight %, or less than 3.7 weight %, or less than 3.5 weight %, based on the total weight of the antiperspirant/deodorant composition. In various tests, the tackiness was determined by an expert sensory panel comprised of at least 10 trained panelists who assess the skin feel properties of the formulas. One of the product characteristics measured in the tests, both on forearm and axillary, was tackiness. The trained panelists assessed the tackiness of the product formulas by feeling the product with their fingertips at given time intervals and rating the tackiness on a scale of 0 (no tack) to 10 (very tacky).

Ameliorating the wet feeling can also be achieved by providing some structure and body to the formula that the wearer perceives as providing a richness to the formula. In other words, at least partially providing structure and body to the formula that the technical effect of ameliorating or reducing the wet feeling.

In one embodiment, the plant-derived oil may be selected to be partially hydrogenated and have a melting point that may be −15° C. (5° F.) to 38° C. (100° F.). In another embodiment, the melting point may be 26° C. (80° F.) to 35° C. (95° F.). To obtain the desired melting point, the plant-derived oil can be partially hydrogenated, or a blend of non-hydrogenated with partially or fully hydrogenated oils and/or waxes can be used.

In an embodiment of the antiperspirant/deodorant composition, the plant-based oil may be a partially hydrogenated soybean oil in an amount of 5% or less by weight, based on the total weight of the composition. In another embodiment of the antiperspirant/deodorant composition, the plant-based oil comprises a partially hydrogenated soybean oil with a melting point of 26 to 38° C.

In one embodiment, the plant-based oil may be a partially hydrogenated soybean oil having an iodine value in the range of 75 to 80. Iodine value can be measured according to ASTM D5554-95 (2006). This partially hydrogenated soybean oil can be obtained from Cargill under the product designation S-500.

Another benefit of using a partially hydrogenated plant oil such as soybean oil in an emulsion is that it can provide structure, in the form of increased viscosity, to the antiperspirant/deodorant composition. Viscosity or structure of a liquid antiperspirant/deodorant composition was measured in mPas (centipoise) by a Brookfield Viscometer at 23° C. using spindle 4 at an RPM setting of 20. In an embodiment, the antiperspirant/deodorant composition has a viscosity in the range of 600 to 4500 mPa, or 700 to 4000 mPa, or 900 to 3000 mPa, or 1500 to 3000 mPa, measured at 23° C. In another embodiment, the antiperspirant/deodorant composition, as disclosed herein above, that further may include a film forming polymer as a zinc substantivity enhancer, can have a viscosity in the range of 500-30,000 mPa.

An additional benefit of using a partially hydrogenated plant oil such as soybean oil within the present disclosure is that it increases the ease of fragrancing or adding fragrance to the antiperspirant/deodorant compositions. The reduced level of malodor formed during the aging of the composition when formulating with partially hydrogenated plant oils allows the fragrance to act only or mostly for pleasant hedonic purposes without having to also cover a malodor. Partially hydrogenated plant oils have a lower iodine value, which corresponds to fewer double bonds. The reduced number of double bonds provides a lower propensity for fragrance degradation, i.e., malodor.

In an embodiment of the antiperspirant/deodorant composition, the oil-in-water emulsion base further may include mineral oil and/or synthetic oil. Any suitable mineral oil that may be colorless, odorless, a mixture of higher alkanes from a mineral source, particularly a distillate of petroleum can be used. Suitable synthetic oils may include, but are not limited to Group IV base oils and Group V base oils. A Group IV base oil may be a poly-alpha-olefin (or poly-α-olefin, abbreviated as PAO), a polymer made by polymerizing an alpha-olefin. Group V base oils may be defined by API as any other type of oil other than mineral oils or PAO lubricants. Synthetics Esters may be the most famous synthetics in Group V, which may be 100% synthetic chemical compounds consisting of a carbonyl adjacent to an ether linkage. They may be derived by reacting an oxoacid with a hydroxyl compound such as an alcohol or phenol. Esters may usually be derived from an inorganic acid or organic acid in which at least one —OH (hydroxyl) group may be replaced by an —O-alkyl (alkoxy) group, most commonly from carboxylic acids and alcohols. That is to say, esters may be formed by condensing an acid with an alcohol, or Semi-synthetic blends of synthetic oils and mineral oils.

Water

The antiperspirant/deodorant composition of the present disclosure also may include water to form the oil-in-water emulsion base. Water may be present in an any suitable amount capable of producing a stable emulsion to make a 100% by weight composition after all of the materials, including any optional materials, may be added to the composition in their desired weight percentages. In certain embodiments, the amount of water may be at least 20%, 30%, 40%, 50%, 60%, 70%, 80%, or 85% by weight of the composition.

The total solids of the composition is, for example, the amount of non-volatile materials in the composition. The total solids of the composition can be measured by a CEM Smart System moisture/solids analyzer which uses microwave energy to dry the samples. In one embodiment, the total solids may be less than 25 weight %, based on the total weight of the original, undried composition. In another embodiment, the amount of total solids may be less than 20 weight %, based on the total weight of the undried composition.

Optional Ingredients

The antiperspirant/deodorant compositions of the present disclosure may also include other ingredients. For example, the antiperspirant/deodorant compositions of the present disclosure may include one or more ingredients for achieving and maintaining a desired consistency, one or more ingredients for giving the product a soothing skin feel, one or more antioxidants, one or more fragrances and one or more ingredients for fragrance duration or retention, and additional deodorizing agent. Some ingredients listed herein can provide more than one function to the compositions. For example, certain emollients can act as lipophilic carrier material and a gelling agent at the same time.

Non-limiting examples of ingredients suitable for use as skin soothing agents are, for example, aloe vera leaf extract or juice, chamomile aqueous extract, other herbal extracts and oatmeal. Non-limiting examples astringents may include, for example witch hazel water. The present antiperspirant/deodorant compositions may include one or more of aloe vera leaf extract or juice present in an amount of 0.5 to 10 weight %, witch hazel (also known as witch hazel water) present in an amount of 1 to 10 weight %, and chamomile aqueous extract present in an amount of 1 to 20 weight %, based on the total weight of the antiperspirant/deodorant composition.

Non-limiting examples of ingredients suitable for use as antioxidants are, for example, one or more of tocopherol and its derivatives, butyl hydroxyanisole (BHA), butyl hydroxytoluene (BHT), erythorbic acid, propyl gallate, sodium erythorbate, tertiary butyl hydroquinone (TBHQ), rosemary extract and, more preferably, ascorbic acid and salts thereof. The antioxidant compound may be one or more of tocopherol and its derivatives present in an amount of 0.001 to 0.5 weight %, or butyl hydroxyanisole (BHA) present in an amount of 0.0075 to 0.1 weight %, butyl hydroxytoluene (BHT) present in an amount of 0.005 to 0.02 weight %, erythorbic acid present in an amount of 0.05 to 1 weight %, propyl gallate present in an amount of 0.05 to 1 weight %, sodium erythorbate present in an amount of 0.05 to 1 weight %, tertiary butyl hydroquinone (TBHQ) present in an amount of 0.005 to 0.1 weight %, rosemary extract present in an amount of 0.02 to 0.4 weight %, and ascorbic acid and salts thereof present in an amount of 0.01 to 0.1 weight %, based on the total weight of the antiperspirant/deodorant composition.

The antiperspirant/deodorant compositions of the present disclosure may include natural and synthetic fragrance(s), if a scented product is desired. Fragrances can be used in any suitable amount, such as in the range of 0.01 to 3%, and, for example, at a level of about 1%.

The antiperspirant/deodorant compositions of the present disclosure may also include ingredients suitable for use for fragrance duration or longevity, such as, for example silica shells, polymeric, or other encapsulates compatible with antiperspirant/deodorant base formulation.

The antiperspirant/deodorant compositions of the present disclosure may include additional deodorizing compounds, for example, including but not limited to, capryl glycol, glyceryl laurate, capric triglyceride, present in an amount of 0.1 to 4 weight %, and lemongrass oil present in an amount of 0.01 to 0.1 weight %, based on the total weight of the antiperspirant/deodorant composition.

Additional gelling agent(s) such as, fatty alcohols may be incorporated into the antiperspirant/deodorant compositions of the present disclosure. In one embodiment, the fatty alcohol may be stearyl alcohol or docosyl alcohol (behenyl alcohol).

Various embodiments of the antiperspirant/deodorant compositions of the present disclosure may be suitable for use as roll-on compositions to be stored/dispensed in roll-on type containers or other types of containers from which a viscous liquid can be dispensed, as are known in the art. The components of conventional roll-on containers can be made of various materials and can have different shapes, as is known in the art. For example, the material of the container can be polypropylene, polyethylene terephthalate (PET), high-density polyethylene or glass. The applicator may be usually a hollow ball made of polypropylene. The ball's diameter can vary from 10 to 36 mm, depending on the design of the container. The ball can be assembled directly in the container or with a special insert (ball housing) depending also on the design of the container. The caps can be of different designs (usually made of polypropylene) with smooth or ribbed walls.

Examples of suitable roll-on dispensers may include those described in U.S. Des. Pat. No. 402,550 to Poisson; U.S. Pat. No. 6,132,126 to Sheffer et al (an adjustable applicator); U.S. Pat. No. 4,030,844 to Lench et al; U.S. Pat. No. 4,021,125 to Berghahn et al; U.S. Pat. No. 4,033,700 to Spatz; U.S. Pat. No. 5,553,957 to Dombusch et al; WO 00/64302 to Hindustan Lever Ltd.; and PCT Patent Appl. Publ. No. WO 01/03541 to Chang; all of which are incorporated by reference herein to the extent they describe roll-on dispensers. Domed containers which mimic a roll-on dispenser without a movable ball can also be used to apply the product. Stick type containers with flat or curved heads containing holes thru which the product can be extruded upon dispensing without a movable ball can also be used to apply the product.

Zinc Substantivity

The antiperspirant/deodorant composition provides excess zinc substantivity on skin (e.g., from zinc oxide, or zinc hydroxide, zinc hydroxide ions, or zinc ions) in an amount of at least 8 picoMoles or at least 50 picoMoles per 0.34 $cm^2$ of skin surface, as measured by the method disclosed hereinbelow.

As used herein, the zinc substantivity may be measured by applying a sample of the antiperspirant/deodorant composition onto a sample of pig skin and equilibrating in a hydrated form for 15 hours at approximately 38° C., followed by rinsing the pig skin five times with 100 µl of 0.1 M NaCl solution to simulate perspiration or sweating. A color-changing zinc-sensitive dye solution was then applied to the pig skin and the amount of zinc was determined from the color change. The method of measuring zinc substantivity may be described in details below under the Example section.

Without wishing to be bound by theory, it is believed that the testing for zinc substantivity done on pig skin using an NaCl solution to simulate sweating on human skin may be representative of zinc substantivity provided by the antiperspirant/deodorant composition of the present disclosure on human skin.

In an aspect, there may be a method of reducing apparent perspiration comprising applying the antiperspirant/deodorant composition, as disclosed hereinabove to an axillary area of a person, wherein the antiperspirant/deodorant composition reduces apparent perspiration, wherein the reduction may be in comparison to an antiperspirant/deodorant composition without the zinc oxide.

In another aspect, the antiperspirant and/or deodorant compositions as disclosed hereinabove can be used to increase substantivity of zinc on a skin surface, when tested using methods as disclosed hereinabove.

In yet another aspect, a zinc substantivity enhancer can be used in the antiperspirant/deodorant composition as disclosed hereinabove to increase zinc retention when applied to an axillary area, such as an armpit, wherein the substantivity enhancer may be any suitable hydrophobic film-forming polymer compatible with the oil-in-water emulsion compositions, as disclosed hereinabove. An exemplary hydrophobic film-forming polymer may include a mixture of polyester-10 and propylene glycol dibenzoate.

The antiperspirant and/or deodorant compositions of the present disclosure provide several advantages and improvements over conventional antiperspirant and/or deodorant compositions. First and foremost is that the antiperspirant/deodorant compositions may be free of added aluminum-based antiperspirant actives, as aluminum has been shown to have adverse side effects in some people. Secondly, the antiperspirant/deodorant compositions as disclosed hereinabove provides increased zinc substantivity, which results in a decrease in the amount of zinc oxide needed to be delivered from the antiperspirant/deodorant compositions and hence a decrease in the overall amount of zinc oxide present in the antiperspirant/deodorant compositions, which in turn decreases the cost of manufacture of these antiperspirant/deodorant compositions. Lastly, the use of plant-based oils and non-silicone based emollients provides formula stability, glideability, increased skin softness and moisturization, low residue, and fast drying.

In yet another aspect, a zinc substantivity enhancer can be used in the antiperspirant/deodorant composition as disclosed hereinabove to increase zinc retention when applied to an axillary area, such as an armpit, wherein the substantivity enhancer may be a film-forming polymer composition comprising PVM/MA decadiene crosspolymer.

EXAMPLES

Testing Method for Zinc Substantivity

The zinc substantivity was measured by applying a sample of the antiperspirant/deodorant composition to be tested onto the outer side, referred to as the stratum corneum, of a sample of pig skin resulting in 5.88 μl/cm$^2$ of the antiperspirant composition on the pig skin and equilibrating in a hydrated form for 15 hours at approximately 38° C. The pig skin sample was in a plug shape, approximately 0.66 cm in diameter, and placed in a standard 96 well cultured plate for the experiments. The pig skin sample was then rinsed five times with 100 μl of 0.1 M NaCl solution to simulate perspiration or sweating. A color-changing zinc-sensitive dye solution [4-(2-Pyridylazo)resorcinol] was then applied to the sample after rinsing with 0.1 M NaCl and then the color change was measured using photographic techniques. Images were captured at two minute intervals for up to 7 hours and the concentration of the zinc was measured by following the development of a red color in the solution with time and correlating against standard curves. The standard curves were generated by combining known amounts of zinc ion and dye and measuring appropriate color change. The amount of desorbed zinc was determined using the colorimetric photography method and analyzed using a multivariant ANOVA for a subset of the time determined by the maximum amount of zinc that can be detected by the dye in solution using the standard curve.

Example 1: Preparation of Aluminum-Free Antiperspirant/Deodorant Composition Comprising Zinc Oxide The aluminum-free antiperspirant/deodorant composition comprising added zinc oxide is an oil in water emulsion consisting of an aqueous phase and an oil phase. The process of making such a formulation is described below:

To make the aqueous phase: DI water was added to a beaker and heated up to 70° C. Then, steareth-20 and glycerin were added and mixed until dissolved. At last, caprylyl glycol was added and mixed for 5 min.

To make the oil phase: steareth-2, soybean oil, diisopropyl adipate and neopentyl glycol were added to a separate beaker and heated to 60° C. while stirring.

To create the Emulsion: The oil phase was added to the aqueous phase while homogenizing at 55 rpm for 3 min with the Greeco homogenizer. While homogenizing, zinc oxide was added. Cooled batch to 30° C. after homogenizing.

Another composition using the method described above was used, except that no esters were used and the ingredients used and their amounts used are shown in Table 1.

Table 1 Shows a Typical Composition Comprising Zinc Oxide in Accordance with the Present Disclosure

| Aluminum-free Antiperspirant/deodorant composition | Example 1.1 Weight % | Example 1.2 Weight % |
|---|---|---|
| Zinc Oxide | 2 | 2 |
| Steareth-20 | 2.5 | 2.5 |
| Stereath-2 | 3 | 3 |
| Glycerin | 4 | 4 |
| Hydrogenated Soybean oil | 4 | 4 |
| Caprylyl Glycol | 0.6 | 0.6 |
| Diisopropyl Adipate | 2.5 | 0 |
| Neopentyl Glycol Diethyhexanoate | 1.2 | 0 |
| Water | Q.S. | Q.S. |

Comparative Example A: Preparation of a Modified Commercially Available Aluminum-Free Antiperspirant/Deodorant Composition Comprising Zinc Oxide A method similar to that used for Example 1 was used except that the ingredients used and their amounts used are shown in Table 2. The composition shown in Table 2 is a non-Al antiperspirant comprising zinc oxide and a silicone-based emollient, for comparison with the antiperspirant/deodorant compositions of the present disclosure.

TABLE 2

| Aluminum-Free Antiperspirant/deodorant Composition comprising silicone-based emollient | Weight % |
|---|---|
| Zinc Oxide | 2 |
| Steareth-21 | 1.5 |
| Stereath-2 | 3.2 |
| Glycerin | 4 |
| PPG-15 STEARYL ETHER | 3.5 |
| CYCLOMETHICONE (CYCLOPENTASILOXANE (D5 > 96%) | 3 |
| Dimethicone 200/50CS | 0.5 |
| Caprylyl Glycol | 0.3 |
| BHT Food Grade (Sanex) | 0.05 |
| Water | Q.S. |

Zinc Substantivity Measurement

The zinc substantivity was measured as discussed above. Table 3 provides the summary of the result: pM of zinc oxide recovered as a function of various aluminum-free compositions. LSM refers to the Least Square Mean amount of zinc, as calculated with the multivariant ANOVA.

TABLE 3

| Sample | Antiperspirant/Deodorant Composition | LSM pM Recovered Zn | P ≤ 0.05 |
|---|---|---|---|
| Example 1.1 | Aluminum-free | 3.83 | B |
| Example 1.2 | Aluminum-free and Ester-free (no adipate or hexanoate) | 4.70 | A |
| Comparative Example A | Aluminum-free with silicone-based emollient and Roll-on Base | 3.29 | C |

Table 3 show an ANOVA of zinc substantivity with respect to specific oil/water emulsion bases. It is clearly seen that the aluminum-free antiperspirant/deodorant composition (Table 1, Al-free) of Examples 1.1 and 1.2 deposits significantly more substantive zinc layer than the aluminum-free antiperspirant/deodorant composition comprising zinc oxide and silicone-based emollient (Table 3, Comparative Example A). The deposition and substantivity of zinc after rinsing is therefore, higher with the aluminum-free antiperspirant/deodorant composition of the present disclosure (Example 1.1 and 1.2) than expected in comparison to antiperspirant/deodorant composition with silicone-based emollient (Comparative Example A). Without being bound by theory, it is hypothesized that the Comparative Example A contains a dimethicone that reduces the substantivity of the zinc oxide as compared to the aluminum-free antiperspirant/deodorant compositions free of any added dimethicone.

As shown in the Table 3 above, the deposition and substantivity of zinc after rinsing is higher with the aluminum-free antiperspirant/deodorant composition comprising no ester (Example 1.2) of the present disclosure in comparison to the aluminum-free antiperspirant/deodorant composition comprising esters (Example 1.1). Even though the presence of ester decreased zinc substantivity, the added esters provided other benefits that more than compensated for the decrease in zinc substantivity. The esters were found to provide enhanced sensory benefits in Example 1.1 without the use of dimethicone. The esters also helped the formula's spreadability and reduced the feeling of being wet. The esters were also found to decrease the drying time.

Example 2: Effect of Steareth-2 on the Zinc Substantivity

A procedure similar to that described in Example 1 was used except that the amount of Steareth-2 in the antiperspirant/deodorant composition was changed from 1 weight % to 4 weight % and the amount of water was changed accordingly to maintain the total amount to 100 weight %. Table 4 shows compositions used and the zinc substantivity as a function of the amount of Steareth-2.

Table 4 Summarizes the Effect of the Amount of Steareth-2

| | Amounts in weight % | | | | | | |
|---|---|---|---|---|---|---|---|
| Example | 2.1 | 2.2 | 2.3 | 2.4 | 2.5 | 2.6 | 2.7 |
| Zinc Oxide | 2 | 2 | 2 | 2 | 2 | 4 | 4 |
| Steareth-2 | 1.0 | 2.5 | 4.0 | 2.5 | 2.5 | 1 | 4 |
| Steareth-20 | 2.5 | 2.5 | 2.5 | 1 | 4 | 4 | 1 |
| Glycerin | 4 | 4 | 4 | 4 | 4 | 4 | 4 |
| Diisopropyl Adipate | 4 | 4 | 4 | 4 | 4 | 1 | 1 |
| Neopnetyl Glycol Diethylhexanoate | 1.75 | 1.75 | 1.75 | 1.75 | 1.75 | 3.5 | 3.5 |
| Soybean oil with BHT | 4.0 | 4.0 | 4.0 | 4.0 | 4.0 | 4.0 | 4.0 |
| Capryl Glycol | 0.6 | 0.6 | 0.6 | 0.6 | 0.6 | 0.6 | 0.6 |
| DI Water | Q.S. | Q.S. | Q.S. | Q.S. | Q.S. | Q.S. | Q.S. |
| pH | 6.72 | 7.31 | 6.39 | 6.46 | 6.92 | 6.87 | 6.51 |
| Viscosity (cP) | 140 | 2400 | 3720 | 1220 | 150 | 30 | 3450 |
| Zinc Substantivity (picoMoles) | 5.49 | 12.72 | 18.62 | 8.51 | 6.79 | 15.29 | 15.93 |

As shown in the table 4 above, Examples 2.1-2.3 shows that while keeping amounts of zinc oxide and Steareth-20 constant, increasing the amount of Steareth-2 from 1 to 4 weight % resulted in a dramatic increase in zinc substantivity from 5.5 to 18.6 picoMoles.

Comparing Examples 2.4 with 2.2 and 2.5, shows the effect of Steareth-20 on zinc substantivity. It should be noted that as the amount of stereath-20 is increased from 1 to 4 weight % at constant amount of Stearate-2 and zinc oxide, the zinc substantivity changed from 8.5 to 12.7 to 6.8 picoMoles, showing that increasing the concentration of steareth-20, especially above 2.5 weight % can lead to a decrease in zinc substantivity.

Furthermore, comparing 2.6 with 2.7 shows that increasing the ratio of Steareth-2:Steareth-20 from 1:4 to 4:1 results in an increase in zinc substantivity from 15.3 to 15.9 picoMoles.

This effect of Steareth-2 alone and in combination with Steareth-20 on the substantivity of zinc is an unexpected and surprising result.

Example 3: Effect of Zinc Oxide on the Zinc Substantivity

A procedure similar to that described in Example 1 was used except that the amount of zinc oxide in the antiperspirant/deodorant composition was changed from 0 to 10 weight % and the amount of water was changed accordingly to maintain the total amount to 100 weight %. Table 5 shows compositions used and zinc substantivity.

Table 5 Summarizes the Effect of the Amount of Zinc

| | Amounts in weight % | | | | | | |
|---|---|---|---|---|---|---|---|
| Example | 3.1 | 3.2 | 3.3 | 3.4 | 3.5 | 3.6 | 3.7 |
| Zinc Oxide | 0.0 | 0.5 | 1.0 | 1.5 | 2.0 | 5.0 | 10.0 |
| Steareth-2 | 2.5 | 2.5 | 2.5 | 2.5 | 2.5 | 2.5 | 2.5 |
| Steareth-20 | 2.5 | 2.5 | 2.5 | 2.5 | 2.5 | 2.5 | 2.5 |
| Glycerin | 4.0 | 4.0 | 4.0 | 4.0 | 4.0 | 4.0 | 4.0 |
| Diisopropyl Adipate | 4.0 | 4.0 | 4.0 | 4.0 | 4.0 | 4.0 | 4.0 |
| Neopnetyl Glycol Diethylhexanoate | 1.8 | 1.8 | 1.8 | 1.8 | 1.8 | 1.8 | 1.8 |
| Soybean oil with BHT | 4.0 | 4.0 | 4.0 | 4.0 | 4.0 | 4.0 | 4.0 |
| Capryl Glycol | 0.6 | 0.6 | 0.6 | 0.6 | 0.6 | 0.6 | 0.6 |
| Water | Q.S. | Q.S. | Q.S. | Q.S. | Q.S. | Q.S. | Q.S. |
| Zinc Substantivity (picoMoles) | 1.3 | 3.4 | 4.5 | 5.4 | 5.6 | 5.8 | 6.1 |
| $P \leq 0.05$ | A | B | C | D | D, E | D, E | E |

As shown in the Table 5, as the amount of zinc is increased from 0 to 4 weight %, the zinc substantivity was found to increase. the zinc substantivity is not linearly correlated to the amount of zinc oxide. Beyond 1.5 weight %, the zinc substantivity is almost constant and does not vary much with a further increase in the amount of zinc oxide. This suggests that one does not need to apply as much zinc oxide when delivered in the oil-in-water base compositions of the present disclosure to retain a higher level of zinc oxide on the skin after rinsing.

Example 4: Effect of Hydrophobic Polymer on the Zinc Substantivity

A procedure similar to that described in Example 1 was used except that a mixture of polyester-10 and propylene glycol dibenzoate (PGDB), in an amount of 0.15 to 6 weight % was added to the antiperspirant/deodorant composition was changed from 0 weight % to 10 weight % and the amount of water was changed accordingly to maintain the total amount to 100 weight %. Table 7 shows composition used and zinc substantivity.

Table 6 Summarizes the Effect of the Amount of Hydrophobic Polymer (Polyester-10+PGDB)

| Sample # | % ZnO | Polyester-10 + PGDB | Ratio of zinc oxide/ (Polyester-10 + PGDB) | WATER | GLYC- ERIN | STEARETH-2 | Steareth-20 | Caprylyl Glycol | Diisopropyl Adipate | Neopentyl glycol Diethylhexanoate | Hydrogenated Soybean oil (55) with BHT | mean pM Zn Recovered |
|---|---|---|---|---|---|---|---|---|---|---|---|---|
| 4.1 | 10.0 | 0.0 | | Q.S. | 4.0 | 3.0 | 2.5 | 0.6 | 2.5 | 1.2 | 4.0 | 33.54 |
| 4.2 | 10.0 | 6.0 | 1.67 | Q.S. | 4.0 | 3.0 | 2.5 | 0.6 | 2.5 | 1.2 | 4.0 | 45.79 |
| 4.3 | 5.0 | 0.0 | | Q.S. | 4.0 | 3.0 | 2.5 | 0.6 | 2.5 | 1.2 | 4.0 | 22.51 |
| 4.4 | 5.0 | 3.0 | 1.67 | Q.S. | 4.0 | 3.0 | 2.5 | 0.6 | 2.5 | 1.2 | 4.0 | 40.25 |
| 4.5 | 2.5 | 1.5 | 1.67 | Q.S. | 4.0 | 3.0 | 2.5 | 0.6 | 2.5 | 1.2 | 4.0 | 36.73 |
| 4.6 | 2.5 | 3.0 | 0.83 | Q.S. | 4.0 | 3.0 | 2.5 | 0.6 | 2.5 | 1.2 | 4.0 | 31.05 |
| 4.7 | 2.0 | 0.0 | | Q.S. | 4.0 | 3.0 | 2.5 | 0.6 | 2.5 | 1.2 | 4.0 | 21.55 |
| 4.8 | 2.0 | 1.3 | 1.50 | Q.S. | 4.0 | 3.0 | 2.5 | 0.6 | 2.5 | 1.2 | 4.0 | 34.93 |
| 4.9 | 1.0 | 0.0 | | Q.S. | 4.0 | 3.0 | 2.5 | 0.6 | 2.5 | 1.2 | 4.0 | 18.52 |
| 4.10 | 1.0 | 0.7 | 1.49 | Q.S. | 4.0 | 3.0 | 2.5 | 0.6 | 2.5 | 1.2 | 4.0 | 15.95 |
| Control | 0.00 | 0.00 | | Q.S. | 4.0 | 3.0 | 2.5 | 0.6 | 2.5 | 1.2 | 4.0 | −0.28 |

As shown in the Table 6 above, the presence of a mixture of polyester-10 and propylene glycol dibenzoate (PGDB) in the composition increases the substantivity of zinc on the pig surface when the ratio of the amounts of zinc oxide to a mixture of polyester-10 and propylene glycol dibenzoate (PGDB) is equal to or greater than 1.50 or 1.67, in a nonlinear fashion when delivered from an antiperspirant/deodorant composition having an oil-in-water emulsion base. Comparing sample 15 with 13 shows that addition of 0.67 weight % of a mixture of polyester-10 and propylene glycol dibenzoate (PGDB) is not sufficient to show an increase in the zinc substantivity. Without wishing to be bound by theory, it is hypothesized that the combination of hydrophobic polymers such as (Polyester-10 dissolved in propylene glycol dibenzoate) with zinc oxide can lead to formation of a surface film which increases water resistance thereby resulting in an increase zinc retention on skin.

Example 5: Effect of Polymer on the Zinc Substantivity

A procedure similar to that described in Example 1 was used except that PVM/MA decadiene crosspolymer in an amount of 0.5 to 2.5 weight % was added to the antiperspirant/deodorant composition with the amount of zinc oxide was changed from 0 to 2 weight % and the amount of water was changed accordingly to maintain the total amount to 100 weight %. Table 7 shows the composition used and zinc substantivity.

Table 7 Summarizes the Effect of the Amount of Film Forming Polymer (PVM/MA Decadiene Crosspolymer)

| | Zinc Oxide | PVM/MA decadiene crosspolymer | Ratio of ZnO/ PVM/MA decadiene crosspolymer | pH | NaOH (50%) | HCl (31%) | Glycerin | Steareth-2 | Steareth-20 |
|---|---|---|---|---|---|---|---|---|---|
| Control | 0 | 0 | — | 7.32 | 0 | 0 | 4 | 3 | 2.5 |
| 5.1 | 1 | 0 | — | 5.51 | 0.8 | 0 | 4 | 3 | 2.5 |
| 5.2 | 1 | 1 | 1.0 | 5.53 | 2.64 | 6 | 4 | 3 | 2.5 |
| 5.3 | 2 | 0 | — | 5.59 | 1 | 21 | 4 | 3 | 2.5 |
| 5.4 | 2 | 1 | 2.0 | 5.57 | 2.64 | 17 | 4 | 3 | 2.5 |
| 5.5 | 1.5 | 0.5 | 3.0 | 5.39 | 1.32 | 2.75 | 4 | 3 | 2.5 |
| 5.6 | 1.5 | 0.5 | 3.0 | 6.28 | 1.7 | 2.75 | 4 | 3 | 2.5 |
| 5.7 | 1.5 | 1 | 1.5 | 6.3 | 3.4 | 3 | 4 | 3 | 2.5 |
| 5.8 | 2 | 0.5 | 4.0 | 6.14 | 1.7 | 5 | 4 | 3 | 2.5 |
| 5.9 | 1 | 1 | 1.0 | 6.99 | 3.84 | 2 | 4 | 3 | 2.5 |
| 5.10 | 2 | 1 | 2.0 | 6.99 | 3.84 | 0.75 | 4 | 3 | 2.5 |
| 5.11 | 2 | 0 | — | 7.86 | 1.25 | 0.5 | 4 | 3 | 2.5 |
| 5.12 | 2 | 2.5 | 0.8 | 8.01 | 10.92 | 0 | 4 | 3 | 2.5 |

| | Capryl Glycol | Diisopropyl Adipate | Neopentyl Glycol Diethylhexanoate | Hydrogenated Soybean Oil with BHT | Demineralized H2O | pM Zn Recovered (LSM) | $p < 0.05$ | Viscosity (mPa) |
|---|---|---|---|---|---|---|---|---|
| Control | 0.6 | 2.5 | 1.2 | 4 | Q.S. | 3.23 | J | |
| 5.1 | 0.6 | 2.5 | 1.2 | 4 | Q.S. | 11.32 | I | 1910 |
| 5.2 | 0.6 | 2.5 | 1.2 | 4 | Q.S. | 22.74 | DE | 1610 |
| 5.3 | 0.6 | 2.5 | 1.2 | 4 | Q.S. | 17.03 | H | 2010 |
| 5.4 | 0.6 | 2.5 | 1.2 | 4 | Q.S. | 19.84 | EFG | 2160 |
| 5.5 | 0.6 | 2.5 | 1.2 | 4 | Q.S. | 25.89 | D | 1156 |
| 5.6 | 0.6 | 2.5 | 1.2 | 4 | Q.S. | 21.36 | EF | 1304 |
| 5.7 | 0.6 | 2.5 | 1.2 | 4 | Q.S. | 17.50 | GH | 1770 |
| 5.8 | 0.6 | 2.5 | 1.2 | 4 | Q.S. | 36.79 | AB | 1594 |
| 5.9 | 0.6 | 2.5 | 1.2 | 4 | Q.S. | 18.06 | FGH | 2020 |
| 5.10 | 0.6 | 2.5 | 1.2 | 4 | Q.S. | 29.74 | C | 2646 |
| 5.11 | 0.6 | 2.5 | 1.2 | 4 | Q.S. | 30.43 | C | 2230 |
| 5.12 | 0.6 | 2.5 | 1.2 | 4 | Q.S. | 22.77 | DE | 17120 |

As shown in the Table 7 above, it is clear from comparing Example 5.1 with 5.2 and 5.3 with 5.4, that as the amount of PVM/MA decadiene crosspolymer in the composition increases, the substantivity of zinc on the pig skin surface also increases when delivered from an antiperspirant/deodorant composition having an oil-in-water emulsion base. Examples 5.5-5.12 shows that the zinc substantivity in the presence of the PVM/MA decadiene crosspolymer is dependent upon both pH and viscosity with decreasing with an increase in pH and/or the viscosity. Also, that zinc substantivity increases with an increase in the amount of zinc oxide, as expected. Without wishing to be bound by theory, it is hypothesized that the combination of film forming polymers such as PVM/MA decadiene crosspolymer with zinc oxide can lead to formation of a surface film which increases water resistance thereby resulting in an increase zinc retention on skin.

Example 6

Test antiperspirant/deodorant compositions including varying amounts of zinc oxide were tested for stinging, burning, and tingling. Particularly, antiperspirant compositions of Example 1.1 (2 weight % ZnO), Example 5.6 (1.5 weight % ZnO), a control (0 weight % ZnO), and two additional test compositions Examples 6.1 and 6.2 (1.1 weight % ZnO) were tested for stinging, burning, and tingling. The new test antiperspirant/deodorant compositions were prepared by combining the components/ingredients of Table 8.

TABLE 8

Test Antiperspirant/Deodorant Compositions 6.1 And 6.2

| Ingredients/Components | Example 6.1 Weight % | Example 6.2 Weight % |
| --- | --- | --- |
| Zinc Oxide | 1.1 | 1.1 |
| Steareth-21 | 1.5 | 1.5 |
| Stereath-2 | 3.2 | 3.2 |
| Sodium Hydroxide | 0.2 | — |
| Cyclomethicone | 2 | 2 |
| Dimethicone | 0.5 | 0.5 |
| Caprylyl Glycol | 0.6 | 0.6 |
| Lactic Acid | — | 0.2 |
| PPG-15 stearyl ether | 3.5 | 3.5 |
| BHT | 0.05 | 0.05 |
| PVM/MA Decadiene Crosspolymer | 1.5 | 1.5 |
| Glycerin | 4 | 4 |
| Water | Q.S. | Q.S. |

To evaluate the stinging, burning, and tingling, 25 females panelists between the ages of 21 and 55 tested each of the antiperspirant compositions. Each of the panelists removed underarm/axillary hair at least three times or more per week via shaving. Each of the 25 female panelists was also identified as a "stinger" from previous studies. Panelists having self-reported skin and/or hand conditions or sensitivities, allergic reactions to antiperspirant products, or pregnant/nursing were excluded from the panel.

Each panelist evaluated one of the samples per day and had at least one day of rest in between each of the samples tested. Products were randomized among the panelists. No more than five hours prior to testing, each of the panelists showered and shaved their underarms. During each of the test sessions, 0.35±0.02 grams of the randomized sample was weighted and placed on a roller of a roll-on package. Each of the panelists then applied the randomized sample and kept their arms naturally at their sides. Each of the panelists was then asked to complete a questionnaire immediately after applications 2, 5, 15, and 30 minutes after application. The results of the stinging, burning, and tingling evaluation are summarized in Table 9.

TABLE 9

Stinging, Burning, and Tingling

| | Control | Example 1.1 | Example 5.6 | Example 6.1 | Example 6.2 |
| --- | --- | --- | --- | --- | --- |
| Zinc Oxide (Weight %) | 0 | 2 | 1.5 | 1.1 | 1.1 |
| PVM/MA Decadiene Crosspolymer (Weight %) | 0.5 | 0 | 0.5 | 1.5 | 1.5 |
| pH | 6 | 5 | 6 | 5.5 | 7.5 |
| Stinging, Burning, Tingling Value | 9 | 15 | 12 | 3.9 | 4.1 |

As indicated in Table 8, reducing the amount of the zinc oxide from 2 weight % to 0 weight % correspondingly decreases the stinging, burning, and tingling. However, as further indicated by the control in Table 8, the stinging, burning, and tingling was not entirely eliminated when zinc oxide was eliminated from the antiperspirant/deodorant compositions. Examples 6.1 and 6.2 demonstrated the effects of varying the amounts of zinc oxide relative to the crosspolymer on the stinging, burning, and tingling. It was surprisingly and unexpectedly discovered that correspondingly reducing the amount of zinc oxide and increasing the amount of the crosspolymer resulted in a significant reduction in the stinging, burning, and tingling. Examples 6.1 and 6.2 also demonstrated that lowering the pH also had some effect on the amount of stinging, burning, and tingling.

What is claimed is:

1. An antiperspirant/deodorant composition comprising:
   an oil-in-water emulsion base comprising: an emulsifier, a plant oil, a polyol, and water; and
   an antiperspirant active dispersed in the oil-in-water emulsion base, wherein the antiperspirant active is free of aluminum antiperspirant actives;
   wherein the zinc antiperspirant active is present in an amount of 0.5-2 weight %, based on the total amount of the antiperspirant/deodorant composition;
   wherein the zinc antiperspirant active is ZnO;
   wherein the composition comprises an emollient consisting of non-silicone based emollient; and
   wherein the composition comprises a substantivity enhancer of the zinc antiperspirant active, wherein the substantivity enhancer is a film-forming polymer composition comprising at least one of a mixture of polyester-10 and propylene glycol dibenzoate; and PVM/MA decadiene crosspolymer.

2. The antiperspirant/deodorant composition of claim 1, wherein the antiperspirant/deodorant composition is free of magnesium actives, and calcium actives.

3. The antiperspirant/deodorant composition of claim 1, wherein the emulsifier is present in an amount of from 0.5 to 5 weight %, based on the total amount of the antiperspirant/deodorant composition.

4. The antiperspirant/deodorant composition of claim 1, wherein the emulsifier comprises a mixture of steareth-2 and steareth-21.

5. The antiperspirant/deodorant composition of claim 1, wherein the emulsifier comprises a mixture of steareth-2 and steareth-20.

6. The antiperspirant/deodorant composition of claim 5, wherein the emulsifier consists essentially of a mixture of steareth-2 and steareth-20, and wherein steareth-2 and steareth-20 are present in a weight ratio of 2.2:1 to 2.5:1.

7. The antiperspirant/deodorant composition of claim 1, wherein the emulsifier further comprises one or more of steareth-2, steareth-4, ceteareth-2, ceteareth-3, ceteareth-4, ceteareth-18, ceteareth-20, and ceteareth-22.

8. The antiperspirant/deodorant composition of claim 1, wherein the non-silicone based emollient is present in an amount of from 0.1 to 6 weight %, based on the total amount of the antiperspirant/deodorant composition.

9. The antiperspirant/deodorant composition of claim 8, wherein the non-silicone based emollient comprises one or more of isopropyl myristate, isopropyl palmitate, isopropyl stearate, isopropyl isostearate, butyl stearate, octyl stearate, hexyl laurate, cetyl stearate, diisopropyl adipate, isodecyl oleate, diisopropyl sebacate, isostearyl lactate, C12-C15 alkyl benzoate, myreth-3 myristate, dioctyl malate, neopentyl glycol diheptanoate, dipropylene glycol dibenzoate, C12-C15 alcohols lactate, isohexyl decanoate, isohexyl caprate, diethylene glycol dioctanoate, octyl isononanoate, isodecyl octanoate, diethylene glycol diisononanoate, isononyl isononanoate, isostearyl isostearate, behenyl behenate, C12-C15 alkyl fumarate, laureth-2 benzoate propylene glycol isoceteth-3 acetate, propylene glycol ceteth-3 acetate, octyldodecyl myristate, and cetyl recinoleate, myristyl myristate, lanolate, paraffin waxes, glycyrrhizic acid, and hydrocyethyl stearate amide.

10. The antiperspirant/deodorant composition of claim 1, wherein the non-silicone based emollient comprises diisopropyl adipate, neopentyl glycol diethylene hexanoate, and mixtures thereof.

11. The antiperspirant/deodorant composition of claim 1, wherein the plant oil comprises one or more of sunflower oil, soybean oil, corn oil, jojoba oil, and methyl and/or ethyl ester derivatives thereof.

12. The antiperspirant/deodorant composition of claim 1, wherein the plant oil comprises a partially hydrogenated soybean oil in an amount of 5% or less by weight.

13. The antiperspirant/deodorant composition of claim 1, wherein the oil-in-water emulsion base further comprises at least one of a mineral oil and a synthetic oil.

14. The antiperspirant/deodorant composition of claim 1, wherein the film-forming polymer composition further comprises at least one of a mixture of polyester-7 and neopentyl glycol diheptanoate; adipic acid/diglycol crosspolymer; trimethylpentanediol/adipic acid/glycerin crosspolymer; trimethylpentanediol/adipic acid copolymer; and capryloyl glycerin/sebacic acid copolymer.

15. The antiperspirant/deodorant composition of claim 1, wherein the antiperspirant/deodorant composition provides substantive zinc in an amount of at least 8 picoMoles per 0.34 cm2 of a skin surface, as measured by the method disclosed herein.

16. The antiperspirant/deodorant composition of claim 1, wherein the non-silicone based emollient is a mixture of diisopropyl adipate and neopentyl glycol diethyhexanoate.

17. A method of reducing apparent perspiration comprising applying the antiperspirant/deodorant composition of any preceding claim to an axillary area of a person, wherein the antiperspirant/deodorant composition of claim 1 reduces apparent perspiration.

* * * * *